(12) United States Patent
Bishop et al.

(10) Patent No.: US 6,573,256 B2
(45) Date of Patent: Jun. 3, 2003

(54) METHOD OF INHIBITING ANGIOGENESIS USING ACTIVE VITAMIN D ANALOGUES

(75) Inventors: Charles W. Bishop, Madison, WI (US); Richard B. Mazess, Madison, WI (US)

(73) Assignee: Bone Care International, Inc., Middleton, WI (US)

( * ) Notice: Subject to any disclaimer, the term of this patent is extended or adjusted under 35 U.S.C. 154(b) by 0 days.

(21) Appl. No.: 09/891,805

(22) Filed: Jun. 26, 2001

(65) Prior Publication Data

US 2002/0019375 A1 Feb. 14, 2002

Related U.S. Application Data

(60) Continuation-in-part of application No. 09/596,149, filed on Feb. 23, 1998, which is a division of application No. 08/781,910, filed on Dec. 30, 1996, now Pat. No. 5,763,429.

(51) Int. Cl.$^7$ .......................... A61K 31/59; A01N 45/00
(52) U.S. Cl. ........................................ 514/168; 514/167
(58) Field of Search .................................. 514/168, 167

(56) References Cited

U.S. PATENT DOCUMENTS

| | | |
|---|---|---|
| 2,383,446 A | 8/1945 | Calcott et al. |
| 3,697,559 A | 10/1972 | DeLuca et al. |
| 3,741,996 A | 6/1973 | DeLuca et al. |
| 3,907,843 A | 9/1975 | DeLuca et al. |
| 4,195,027 A | 3/1980 | DeLuca et al. |
| 4,202,829 A | 5/1980 | DeLuca et al. |
| 4,225,596 A | 9/1980 | DeLuca et al. |
| 4,234,495 A | 11/1980 | DeLuca et al. |
| 4,260,549 A | 4/1981 | DeLuca et al. |
| 4,362,710 A | 12/1982 | Watanabe |
| 4,391,802 A | 7/1983 | Suda et al. |
| 4,508,651 A | 4/1985 | Baggiolini et al. |
| 4,554,106 A | 11/1985 | DeLuca et al. |
| 4,555,364 A | 11/1985 | DeLuca et al. |
| 4,588,716 A | 5/1986 | DeLuca et al. |
| 4,661,294 A | 4/1987 | Holick et al. |
| 4,670,190 A | 6/1987 | Hesse et al. |
| 4,689,180 A | 8/1987 | DeLuca et al. |
| 4,698,328 A | 10/1987 | Neer et al. |
| 4,833,125 A | 5/1989 | Neer et al. |
| 4,866,048 A | 9/1989 | Calverley et al. |
| 5,063,221 A | 11/1991 | Nishii et al. |
| 5,104,864 A | 4/1992 | DeLuca et al. |
| 5,157,135 A | 10/1992 | Tsuji et al. |
| 5,372,996 A | 12/1994 | Labrie |
| 5,403,831 A | 4/1995 | DeLuca et al. |
| 5,448,120 A | 9/1995 | Schaule et al. |
| 5,486,636 A | 1/1996 | DeLuca et al. |
| 5,488,120 A | 1/1996 | DeLuca et al. |
| 5,602,116 A | 2/1997 | Knutson et al. |
| 5,763,428 A | 6/1998 | Knutson et al. |
| 5,763,429 A | 6/1998 | Bishop et al. |
| 5,786,348 A | 7/1998 | Bishop et al. |
| 5,789,345 A | 8/1998 | Knutson et al. |
| 5,789,397 A | 8/1998 | Bishop et al. |
| 5,801,164 A | 9/1998 | Knutson et al. |
| 6,025,346 A | 2/2000 | Knutson et al. |
| 6,166,000 A | 12/2000 | Bishop et al. |
| 6,211,168 B1 | 4/2001 | Bishop et al. |
| 6,087,350 A1 | 7/2001 | Johnson et al. |

FOREIGN PATENT DOCUMENTS

| | | |
|---|---|---|
| BE | A-877 356 | 10/1979 |
| EP | 0197514 | 10/1986 |
| EP | A-0 390 097 | 10/1990 |
| EP | 0 503 630 A1 | 3/1992 |
| EP | 0 562 497 A1 | 9/1993 |
| EP | 0 664 287 A1 | 7/1995 |
| WO | 8404527 | 11/1984 |
| WO | WO 87/00834 | 2/1987 |
| WO | WO 90/10620 | 9/1990 |
| WO | WO 92/05130 | 4/1992 |
| WO | WO 92/12165 | 7/1992 |
| WO | WO 92/21355 | 12/1992 |
| WO | WO 93/14763 | 8/1993 |
| WO | WO 94/05630 | 3/1994 |
| WO | WO 94/16711 | 8/1994 |
| WO | WO 96/40153 | 12/1996 |
| WO | WO 96/40154 | 12/1996 |
| WO | WO 97/23242 | 7/1997 |
| WO | WO 98/56387 | 12/1998 |
| WO | WO 98/56389 | 12/1998 |
| WO | WO 99/16451 | 4/1999 |
| WO | WO 99/49027 | 9/1999 |
| WO | WO 99/49870 | 10/1999 |
| WO | WO 00/03700 | 1/2000 |
| WO | WO 01/22974 | 4/2001 |
| WO | WO 01/64251 A2 | 9/2001 |

OTHER PUBLICATIONS

L.E. Reeve et al., "Biological Activity of 1 α–hydroxy Vitamin $D_2$ in the Rat" *Arch. Biochem. Biophys.* 186, 1, Feb. 1978, pp. 164–167.

Sjoden et al., "Effects of 1 $OHD_2$ on Bone Tissue" *Acta. Endocrinol.* (Copenh.) 16, 4, Aug. 1984, pp. 564–568.

N. Brautbar, "Osteoporosis: Is 1,25–$(OH)_2D$ of Value in Treatment?" *Nephron* 44, 1986, pp. 161–166.

Y. Tanaka et al., *Endocrinology*, 1973, 92, pp. 417–422.

O.H. Sorenson et al., *Clin. Endocrinol.*, 1977, 7, pp. 169S–175S.

V. Hoikka et al., *Acta. Med. Scand.*, 1980, 207, pp. 221–224.

Brown et al., *Lancet*, 1984, 1, pp. 1091–1093.

J. Podenphant et al., *Acta Med Scand.*, 1985, 218, pp. 329–333.

(List continued on next page.)

*Primary Examiner*—Theodore J. Criares
(74) *Attorney, Agent, or Firm*—Michael Best & Friedrich LLP; Teresa J. Welch; Jeffrey D. Peterson

(57) ABSTRACT

Methods utilizing active vitamin D analogs for the inhibition of angiogenesis associated with malignant and neoplasmic cells. Methods comprise the application of an effective amount of a hypocalcemic vitamin D compound to inhibit the angiogenesis of malignant cells, inducing the apoptosis of malignant cells, and regressing the growth of tumorous cells.

34 Claims, No Drawings

OTHER PUBLICATIONS

Caniggia et al., *Calif Tissue Int.*, 1986, 38, pp. 328–332.
Duda et al., *J. Clinic Invest.*, 1987, 79, pp. 1249–1253.
Sommerfeldt et al., *J. Nutr.*, 1983, 11, pp. 2595–2600.
Zerwebh et al., *J. Clin. Endocrinol. Metabol.*, 1985, 60, pp. 615–617.
Horst et al., *Anal. Biochem.*, 1981, 116, pp. 189–203.
Horst et al., *Biochem. J.*, 1982, 204, pp. 185–189.
Folders et al., *Osteoporosis*, 1987, C. Christianson et al. (eds.) Osteopress Aps, Copenhagen, pp. 971–973.
Guidelines for the Clinical Evaluation of Drugs Used in the Treatment of Osteoporosis, HEW (FDA) 80–3094, pp. 5–6 (1979).
J.A. Kanis et al., Guidelines for Clinical Trials in Osteoporosis, A Position Paper of the European Foundation for Osteoporosis, *Osteoporosis Int.*, 1991, 1, pp. 182–188.
C. Christiansen et al., "Prevention of Early Postmenopausal Bone Loss: Controlled 2–Year Study in 315 Normal Females," *Europ J Clin Invest, 1980, 10*, pp. 273–279.
J.M. Pouilles et al., "Prevention of Early Postmenopausal Bone Loss with 1 α–Hydroxy Vitamin $D_3$, A Three–Year Prospective Study," *Clin Rheumatol.*, 11, 1992, 4, pp. 492–497.
M.F. Holick et al., *Proc. Natl. Acad. Sci. USA* 68, 803–804 (1971).
G. Jones et al., *Biochemistry* 14, 1250–1256 (1975).
M.F. Holick et al., *Science* 180, 190, 191 (1973).
H.Y. Lam et al., *Science* 486, 1038–1040 (1974).
S.M. Ott, C.H. Chestnut, *Annals of Int. Med.* 1989, 110:267–274.
J.C. Gallagher et al., *Annals of Int. Med.* 1990, 113:649–655.
J. Aloia et al., *Amer. J. Med.* 84:401–08 (1988).
M. Shiraki et al., *Endocrinol Japan* 32, 305–315 (1985).
G.F. Jensen et al., *Clin. Endocrinol.* 16, 515–524 (1982).
C. Christiansen et al., *Eur. J. Clin. Invest.* 11, 305–309 (1981).
O.H. Sorensen et al., *Clin. Endocrinol.* 7, 169S–175S (1977).
H. Orimo et al., *Bone and Mineral* 3, 47–52 (1987).
G. Sjoden et al., *J. Nutr.* 114, 2043–2046 (1984).
G. Sjoden et al., *Proc. Soc. Exp. Biol. Med.* 178, 432–436 (1985).
J.C. Gallagher et al., *J. Bone Min. Res.*; 1994; 9:607–614.
E. Braunwald et al., *Harrison's Principles of Internal Medicine*: Part Eleven, "Disorders of Bone and Mineral Metabolism," Chapter 335, McGraw–Hill, New York, 1987, pp. 1860–1865.
W. Grab, *Z. Physiol. Chem.*, 243:63–89 (1936).
F.G. McDonald, *J. Biol. Chem.*, 114:IVX (1936).
A. Windaus et al., *Z. Physiol. Chem.*, 247–:185–188 (1937).
DeLuca et al., *Arch. Biochem, Biophys.*, 124:122–128 (1968).
*Merck Index*, S. Budavari (ed.), 11th ed., Merck & Co., Rahway, N.J. (1989) pp. 1579, #9930.
Barton et al., *JCS Perkin I*, 1976, 821–826.
Paaren et al., *J. Org. Chem.*, 1980, 45:3253.

S. Wientroub et al. "The Dichotomy in the Effects of 1, 25 dihydroxy vitamin $D_3$ and 24, 25 dihydroxy vitamin $D_3$ on Bone Gamma–Carboxyglutamic Acid–Containing Protein in Serum and Bone in vitamin D–Deficient Rats," *Calcif, Tissue Int.* (1987) 40:166–172.
Strugnell et al., *Biochem. Pharm.* vol. 40:333–341 (1990).
P.J. Kocienski et al., *J.C.S. Perkins I*, 1290–1293 (1979).
M. Tsuji et al., *Bull. Chem. Soc. Jpn.*, vol. 63, No. 8, 2233–2238 (1990).
D.R. Crump et al., *J.C.S. Perkins Trans. I*, 2731–2733 (1973).
Chemical Abstracts, vol. 113, No. 1, Jul. 1990, Columbus, Ohio, US; abstract No. 6683y, Y. Tachibana, 'Preparation of 1 beta–hydroxyvitamin $D_2$ and $D_3$,' p. 6688; column 2; abstract & JP–A–02 011 563 (Nisshin Flour Milling Co.).
Chemistry Letters, No. 8, Aug. 1985, Tokyo, JP, pp. 1131–1132, H. Nemeto et al., 'A stereoselective synthesis of 1 alpha–hydroxy–vitamin $D_3$'.
F. Sato et al., *Biochim. Biophys. Acta*, vol. 1091 (1991) pp. 188–192.
*Holick, M.F., "Noncalcemic Actions of 1,25–Dihydroxyvitamin $D_3$ and Clinical Applications", *Bone*, vol. 17, 2:107S–110S (1995).
* Knutson, et al., "Metabolism of 1 α–Hydroxyvitamin $D_2$ to activated Dihydroxyvitamin $D_2$ Metabolites Decreases Endogenous 1 α,25–Dihydroxyvitamin $D_3$ in Rats and Monkeys", *Endocrinology*, vol. 136, 11:4749–4753 (1995).
* Majewski, et al., "Inhibition of Tumor Cell–Induced Angiogenisis by Retinoids, 1,25–Dihydroxyvitamin $D_3$ and their Combination", *Cancer Letters*, vol. 75, 35–39 (1993).
Miller et al., "The Human Prostatic Carcinoma Cell Line LNCaP Expresses Biologically Active, Specific Receptors for 1 α,25–Dihydroxyvitamin $D_3$ ₁," 52 *Cancer Res.* (1992) 515–520.
Strugnell et al., "1 α,24(S)–Dihydroxyvitamin $D_2$: a biologically active product of 1 α–hydroxyvitamin $D_2$ made in the human hepatoma, Hep3B," 310 *Biochem. J.* (1995) pp. 233–241.
Skowronski et al., "Actions Of Vitamin $D_3$ Analogs on Human Prostrate Cancer Cell Lines: Comparison with 1,25–Dihydroxyvitamin $D_3$, " 136 *Endocrinology* (1995) 20–26.
Skowronski et al., "Vitamin D and Prostate Cancer: 1,25 Dihydroxyvitamin $D_3$ Receptors and Actions in Human Prostate Cancer Cell Lines," 132 *Endocrinology* (1993) 1952–1960.
Mantell, D.J., Owens, P.E., Bundred, N.J., Mawer, E.B., Canfield, A.E., "1 α,25–Dihydroxyvitamin $D_3$ Inhibits Angiogenesis In Vitro and In Vivo", Circulation Research, Aug. 4, 2000, pp. 214–220.
Beer, et al., "A Phase I Trial of Pulse Calcitriol in Patients with Refractory Malignancies," *Cancer*, vol. 91, No. 12 (Jun. 15, 2001) 2431–2439.
Beer, et al., "Weekly High–Dose Calcitriol and Docetaxel in Advanced Prostate Cancer," *Seminars in Oncology*, vol. 28, No. 4., Suppl 15 (Aug. 2001) 49–55.

METHOD OF INHIBITING ANGIOGENESIS USING ACTIVE VITAMIN D ANALOGUES

CROSS-REFERENCE TO RELATED APPLICATIONS

This application is a continuation-in-part of U.S. application Ser. No. 09/596,149, filed Feb. 23, 1998, pending which is a divisional of U.S. application Ser. No. 08/781,910, filed Dec. 30, 1996, now U.S. Pat. No. 5,763,429, all of which are incorporated herein by reference.

STATEMENT REGARDING FEDERALLY SPONSORED RESEARCH OR DEVELOPMENT

Not Applicable

BACKGROUND OF THE INVENTION

This invention relates generally to a method of inhibiting angiogenesis associated with the hyperproliferation of malignant cells, and in particular, to the use of active forms of vitamin D to inhibit angiogenesis of malignant cells.

Extensive research during the past two decades has established important biologic roles for vitamin D apart from its classic role in bone and mineral metabolism. Specific nuclear receptors for $1\alpha,25$-dihydroxyvitamin $D_3$, the hormonally active form of vitamin D, are present in cells from diverse organs not involved in calcium homeostasis. For example, specific, biologically active vitamin D receptors have been demonstrated in the human prostatic carcinoma cell line, LNCaP, (Miller et al., 52 *Cancer Res.* (1992) 515–520); Vitamin D receptors have also been described for many other neoplastic cells, e.g., carcinomas of the breast and the colon.

It has been reported that certain vitamin D compounds and analogues are potent inhibitors of malignant cell proliferation and are inducers/stimulators of cell differentiation. For example, U.S. Pat. No. 4,391,802 issued to Suda et al. discloses that $1\alpha$-hydroxyvitamin D compounds, specifically $1\alpha,25$-dihydroxyvitamin $D_3$ and $1\alpha$-hydroxyvitamin $D_3$, possess potent antileukemic activity by virtue of inducing the differentiation of malignant cells (specifically leukemia cells) to nonmalignant macrophages (monocytes), and are useful in the treatment of leukemia. Antiproliferative and differentiating actions of $1\alpha,25$-dihydroxyvitamin $D_3$ and other vitamin $D_3$ analogues have been reported with respect to cancer cell lines. More recently, an association between vitamin D receptor gene polymorphism and cancer risk has been reported, suggesting that vitamin D receptors may have a role in the development, and possible treatment, of cancer.

These previous studies have focused exclusively on vitamin $D_3$ compounds. Even though these compounds may indeed be highly effective in promoting differentiation in malignant cells in culture, their practical use in differentiation therapy as anticancer agents is severely limited because of their equally high potency as agents affecting calcium metabolism. At the levels required in vivo for effective use as, for example, antileukemic agents, these same compounds can induce markedly elevated and potentially dangerous blood calcium levels by virtue of their inherent calcemic activity. That is, the clinical use of $1\alpha,25$-dihydroxyvitamin $D_3$ and other vitamin $D_3$ analogues as anticancer agents is precluded, or severely limited, by the risk of hypercalcemia.

Cancerous cells derive from a single cell that has mutated in a way that permits it to escape from the biochemical controls that limit the multiplication of normal cells. Once that cell fails to respond normally to growth inhibitors, it starts to proliferate. When the growing tumor reaches a certain diameter, however, simple diffusion in and out of the tumor tissue no longer suffices to supply oxygen and nutrients and remove waste. Further growth depends on angiogenesis (i.e., the formation of new blood vessels from the existing vascular bed), and the small tumor must produce factors that stimulate the growth of blood vessels. Therefore, the inhibition of angiogenesis, in turn leads to the decrease of proliferation of malignant and neoplastic cells.

Vascular endothelial growth factor (VEGF) is a key mediator of angiogenesis. This growth factor stimulates the endothelial cell proliferation, sprouting, migration and morphogenesis. A recent study has found that $1\alpha,25$-dihydroxyvitamin $D_3$ significantly inhibited vascular endothelial growth factor (VEGF)-induced endothelial cell proliferation. (See "$1\alpha,25$-Dihydroxyvitamin $D_3$ Ihibits Angiogenesis In Vitro and In Vivo", Mantell, D. J., Owens, P. E., Bundred, N. J., Mawer, E. B., Canfield, A. E., Circulation Research, Aug. 4, 2000, pp. 214–220. Incorporated herein by reference). It was also demonstrated that $1\alpha,25$-dihydroxyvitamin $D_3$ induced the regression of sprouting elongated endothelial cells, where the regression was due to the induction of apoptosis within the cell population. As mentioned earlier however, use of such vitamin $D_3$ analogs as anticancer agents is limited due to the inherent calcemic activity of the compounds. Therefore a need exists for compounds with the ability to inhibit angiogenesis of malignant cells but which have less calcemic activity.

BRIEF SUMMARY OF THE INVENTION

The present invention provides a method of inhibiting angiogenesis associated with malignant cells. The method includes use of hypocalcemic active vitamin D compounds to inhibit angiogenesis. The present invention also provides a method of inducing the apoptosis of cancer cells by the use of active vitamin D compounds, and includes a method for treating cancer by regressing tumor cells by the use of active vitamin D compounds.

The foregoing, and other advantages of the present invention, are realized in one aspect thereof in a method of inhibiting angiogenesis associated with malignant cells, comprising treating the cells with an effective amount of a hypocalcemic vitamin D compound. The hypocalcemic vitamin D compound of the present invention include hypocalcemic vitamin D compounds having a hydrocarbon moiety substituted at the C-24 position on the sidechain of the molecule and having a hydroxyl group substituted in at least one of the $C_1$, $C_{24}$ or $C_{25}$ positions.

The hypocalcemic vitamin D compound is an active vitamin D and is suitably represented by the formula (I) described hereafter. Suitable compounds of formula (I), are $1\alpha,24$-dihydroxyvitamin $D_2$, $1\alpha,24$-dihydroxyvitamin $D_4$, $1\alpha,25$-dihydroxyvitamin $D_4$, $1\alpha,25$-dihydroxyvitamin $D_2$, $1\alpha$-hydroxyvitamin $D_2$ and $1\alpha$-hydroxyvitamin $D_4$.

The effective or therapeutic amount of the $1\alpha$-hydroxyvitamin D compound administrable in accordance with the present invention to patients in need on a daily basis per kilogram of body weight ranges from 0.01 µg/kg/day to 2.0 µg/kg/day.

In another aspect of the invention, the apoptosis of cancer cells is accomplished by a method comprising, administering to patients an effective amount of a hypocalcemic vitamin D compound to induce the apoptosis of cancer cells.

In yet another aspect of the invention, a method for treating cancer by regressing tumor cells is disclosed, comprising administering to patients an effective amount of a hypocalcemic vitamin D compound to induce the regression of cancer cells.

In accordance with the present invention, when effective amounts of the hypocalcemic vitamin D compounds are administered to patients with cancer or neoplasms, the proliferative activity of the abnormal neoplastic cells is inhibited or maintained, and cell differentiation is induced, promoted or enhanced, with significantly less hypercalcemia and hypercalciuria than is observed after the same amount of an activated vitamin $D_3$ (e.g., $1\alpha$—OH $D_3$, $1\alpha,25$—$(OH)_2$ $D_3$) is administered in previously known formulations. Thus, the compound in accordance with the present invention has an improved therapeutic index relative to active forms of vitamin $D_3$ analogues. Furthermore, the compounds of the present invention can be administered in doses significantly higher than that of active vitamin $D_3$ analogs due to their lower calcemic effect.

Accordingly, another aspect of the invention is a method of treating human cancer comprising administering to a subject who has cancer an effective amount of active vitamin D compound which has, attained through metabolism in vivo, a vitamin D receptor (VDR) binding affinity substantially equivalent to the binding affinity of $1\alpha,25$-dihydroxyvitamin $D_3$ and a hypercalcemia risk substantially lower that that of $1\alpha,25$-dihydroxyvitamin $D_3$, to decrease or stabilize the cellular abnormal proliferative activity of the cancer.

For treatment for malignant conditions in accordance with the present invention, the active vitamin D is suitably administered alone as an active ingredient in a pharmaceutical composition, or is co-administered with an anticancer agent.

Further, included within the scope of the present invention is the co-administration of a hypocalcemic vitamin D compound with a cytotoxic or anticancer agent. Such agents suitably include antimetabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophasphamide, melphalan, biochoroethylnitrosurea, hydroxyurea), platinum agents (e.g. cisplatin, carboplatin, oxaliplatin, JM-216, CI-973), anthracyclines (e.g., doxrubicin, daunorubicin), antibiolitics (e.g., mitomycin, idarubicin, adriamycin, daunomycin), topoisomerase inhibitiors (e.g., etoposide, camptothecins) or any other cytotoxic agents. (estramustine phosphate, prednimustine).

It is anticipated that the active vitamin D compounds used in combination with various anticancer drugs can give rise to a significantly enhanced cytotoxic effect on cancerous cells, thus providing an increased therapeutic effect. Specifically, as a significantly increased growth-inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the anticancer drugs used alone in larger doses. Possible dose ranges of these co-administered anticancer agents are about 0.1 to 20 mg/kg/day.

Also included within the scope of the present invention is the co-administration of effective dosages of a hypocalcemic vitamin D compound in conjunction with administration of hormones or other agents, e.g., estrogens, which are known to ameliorate bone diseases or disorders. For example, prostate cancer often metastasizes to bone, causing bone loss and associated pain. Such bone agents may include conjugated estrogens or their equivalents, calcitonin, bisphosphonates, calcium supplements, cobalamin, pertussis toxin and boron.

In another aspect, the invention is a pharmaceutical composition which includes an anticancer agent which is an active vitamin D compound; an agent selected from the group consisting of (i) an anticancer agent, (ii) a bone agent, and combinations thereof; and a physiologically acceptable carrier.

Other advantages and a fuller appreciation of specific adaptations, compositional variations, and physical attributes will be gained upon an examination of the following detailed description of preferred embodiments, taken in conjunction with the appended claims.

BRIEF DESCRIPTION OF THE DRAWING(S)

Not Applicable

DETAILED DESCRIPTION OF THE INVENTION

The present invention provides an effective method for inhibiting angiogenesis associated with the hyperproliferation of malignant cells. The present invention also includes therapeutic methods for inhibiting, reducing or stabilizing the hyperproliferative cellular activity of malignant and neoplastic diseases, as well as inducing, enhancing or promoting cell differentiation in the diseased cells. The present invention provides a novel inhibition of angiogenesis of a patient suffering from a hyperproliferative disease with an active hypocalcemic vitamin D compound. The active vitamin D analogue is suitably a hydroxyvitamin D compound e.g. a $1\alpha$-hydroxy vitamin D or a 24-hydroxy vitamin D, and is suitably represented by formula (I) as described hereinbelow. The active vitamin D analogue is provided to the patient without causing dose-limiting hypercalcemia and hypercalciuria, i.e., unphysiologically high and deleterious blood calcium levels and urine calcium levels, respectively, and in fact reduces the hypercalcemia caused by the malignancy. These attributes are achieved through specific chemical properties of the hypocalcemic vitamin D compounds as described.

In accordance with the present invention, when effective amounts of the analogues of the hypocalcemic vitamin D compound are administered to patients with malignant diseases, the angiogenesis of cancerous cells is inhibited, tumorous cells are regressed, cancerous cells undergo apoptosis, and the proliferative activity of the abnormal cells are inhibited, reduced, or stabilized, and cell differentiation is induced, promoted or enhanced, with significantly less hypercalcemia and hypercalciuria than is observed after the same amount of activated vitamin $D_3$ is administered in previously known formulations. Thus, the hypocalcemic vitamin D compounds of the present invention have an improved therapeutic index relative to active forms of vitamin $D_3$ analogues.

It is known that vitamin $D_3$ must be hydroxylated in the C-1 and C-25 positions before it is activated, i.e., before it will produce a biological response. A similar metabolism appears to be required to activate other forms of vitamin D, e.g., vitamin $D_2$ and vitamin $D_4$. Therefore, as used herein, the term "activated vitamin D" or "active vitamin D" is intended to refer to a vitamin D compound or analogue that has been hydroxylated in at least the C-1, C-24 or C-25 position of the molecule and either the compound itself or its metabolites in the case of a prodrug, such as 1α-hydroxyvitamin $D_2$, binds the vitamin D receptor (VDR). For example, "prodrugs" include vitamin D compounds which are hydroxylated in the C-1 position. Such compounds undergo further hydroxylation in vivo and their metabolites bind the VDR.

The term "hypocalcemic vitamin D compound" is in reference to active vitamin D analogs which demonstrate hypocalcemic activity, i.e., substantially less calcemic activity relative to the calcemic activity of 1α,25-dihydroxy vitamin $D_3$. Such compounds include 24-hydroxyvitamin D compounds, 25-hydroxyvitamin D compounds and 1α-hydroxyvitamin D compounds.

Also, as used herein, the term "lower" as a modifier for alkyl, alkenyl acyl, or cycloalkyl is meant to refer to a straight or branched, saturated or unsaturated hydrocarbon radical having 1 to 4 carbon atoms. Specific examples of such hydrocarbon radicals are methyl, ethyl, propyl, isopropyl, butyl, isobutyl, t-butyl, ethenyl, propenyl, butenyl, isobutenyl, isopropenyl, formyl, acetyl, propionyl, butyryl or cyclopropyl. The term "aromatic acyl" is meant to refer to a unsubstituted or substituted benzoyl group.

As used herein, the term "hydrocarbon moiety" refers to a lower alkyl, a lower alkenyl, a lower acyl group or a lower cycloalkyl, i.e., a straight or branched, saturated or unsaturated $C_1$–$C_4$ hydrocarbon radial.

The compound in accordance with the present invention is an active hypocalcemic vitamin D compound. The active vitamin D provided is such that the compound has a hydrocarbon moiety at the C-24 position, e.g. a lower alkyl, alkenyl or acyl group as the C-24 position. Further, the active vitamin D in accordance with the present invention may have an unsaturated sidechain, e.g., there is suitably a double bond between C-22 and C-23, between C-25 and C-26 or between C-26 and C-27.

The hydroxyvitamin D of the present invention preferably has the general formula described in formula (I)

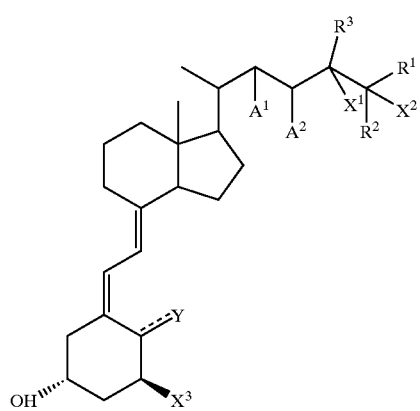

(I)

wherein $A^1$ and $A^2$ each are hydrogen or a carbon—carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, and $X^2$ is hydrogen or hydroxyl, or, may be taken with $R^1$ or $R^2$, to constitute a double bond, and $X^3$ is hydrogen or hydroxyl provided that at least one of $X^1$, $X^2$ and $X^3$ is hydroxyl; and Y is a methylene group if the bond to Y is a double or is a methyl group or hydrogen if the bond to Y is a single bond.

A 1α-hydroxyvitamin D compound of formula (I) is characterized by the general formula (II):

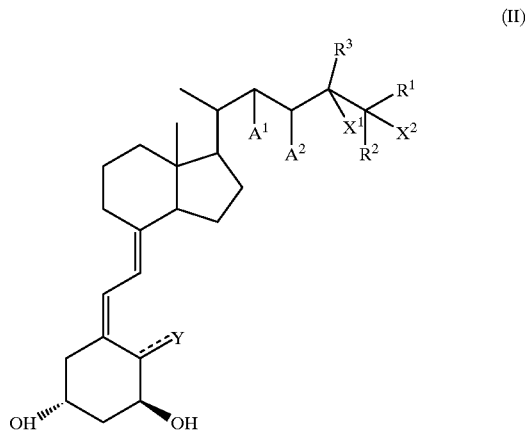

(II)

wherein $A^1$ and $A^2$ each are hydrogen or a carbon—carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, and $X^2$ is hydrogen or hydroxyl, or, may be taken with $R^1$ or $R^2$, to constitute a double bond, and Y is a methylene group if the bond to Y is a double or is a methyl group or hydrogen if the bond to Y is a single bond.

Specific 1α-hydroxyvitamin D compounds in accordance with the present invention are characterized by the general formula (III):

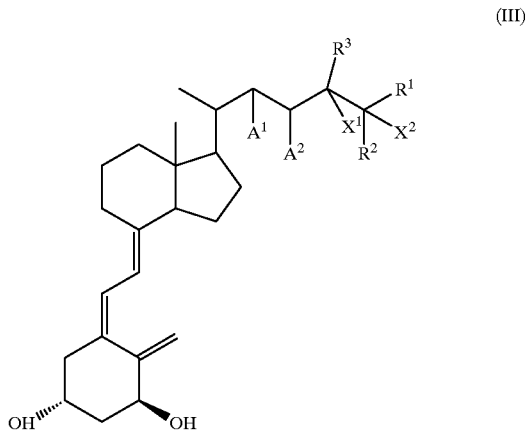

(III)

wherein $A^1$ and $A^2$ each are hydrogen or a carbon—carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, and $X^2$ is hydrogen or hydroxyl, or, may be taken with $R^1$ or $R^2$, to constitute a double bond.

The hypocalcemic vitamin D compounds of formula (I) of the present invention are those that have an effective inhibition effect on the angiogenesis of cancerous cells, but have a lower tendency or inability to cause the undesired side effects of hypercalcemia and/or hypercalciuria i.e. they are hypocalcemic compounds. In other words, the compounds of the present invention can be administered at dosages that allow them to act as angiogenesis inhibition agents when exposed to malignant or other hyperproliferative cells without significantly altering calcium metabolism. This selectivity and specificity of action makes the hypocalcemic vitamin D compounds useful and preferred agents for safely inhibiting angiogenesis of hyperproliferative cells. The compounds of the present invention, thus, overcome the shortcomings of the known active vitamin $D_3$ compounds described above, and can be considered preferred agents for the control angiogenesis of malignant diseases such breast, colon, testicular and prostate cancer, as well as other neoplasms such as pancreatic cancer, endometrial cancer, small cell and non-small cell cancer of the lung (including squamous, adneocarcinoma and large cell types), squamous cell of the head and neck, bladder, ovarian and cervical cancers, myeloid and lymphocyltic leukemia, lymphoma, hepatic tumors, medullary thyroid carcinoma, multiple myeloma, melanoma, retinoblastoma, and sarcomas of the soft tissue and bone, i.e., neoplasms that express a vitamin D receptor.

Suitable active vitamin D compounds of formula (I) include: 1α,24-dihydroxyvitamin $D_2$, 1α,24-dihydroxyvitamin $D_4$, 1α,25-dihydroxyvitamin $D_2$, 1α,25-dihydroxyvitamin $D_4$, 1α-hydroxyvitamin $D_2$, and 1α-hydroxyvitamin $D_4$. Among those compounds of formula (I) that have a chiral center in the sidechain, such as at C-24, it is understood that both epimers (e.g., R and S) and the racemic mixture are within the scope of the present invention.

Thus, the present invention provides a method of inhibiting angiogenesis of malignant cells as well as other hyperproliferative cells such as psoriatic cells with an effective amount of a hypocalcemic vitamin D compound. The effective dosage amount on a daily basis per kilogram of body weight of the patient ranges from about 0.01 μg/kg/day to about 2.0 μg/kg/day. The compounds in accordance with the present invention can be given in a daily dose or episodic dose, e.g., once every 2–6 days once per week. The dose or each day can be a single dose or divided into 2–4 subdoses which can be given, e.g., an hour apart until the total dose is given. The compounds in accordance with the present invention are administered in an amount that raises a serum vitamin D level to a supraphysiological level for a sufficient time to inhibit angiogenesis or induce the hypercalcemic properties of the compounds permit said supraphysiologic levels.

The compounds of formula (I) are valuable for the inhibition of angiogenesis of cancer and neoplasms in a patient suffering therefrom. In particular, the invention is a method for treating a patient suffering from the hyperproliferative cellular effects of cancer and othe neoplasms by administering to the patient a therapeutically effective amount of a compound of formula (I), which is suitably 1α,24-dihydroxyvitamin $D_2$, 1α,24-dihydroxyvitamin $D_4$, 1α,25-dihydroxyvitamin $D_2$, 1α,25-dihydroxyvitamin $D_4$, 1α-hydroxyvitamin $D_2$, and 1α-hydroxyvitamin $D_4$, sufficient to inhibit antiogenesis of the cancer neoplasms. Among those compounds of formula (I) that have a chiral center in the sidechain, such as at C-24, it is understood that both epimers (e.g., R and S) and the racemic mixture are within the scope of the present invention.

The compounds of formula (I) can be prepared as described, e.g., in U.S. Pat. No 5,488,120 issued to Knutson et al., U.S. Pat. Nos. 4,554,106, 4,670,190 and 5,486,636 issued to DeLuca et al., and Strugnell et al., 310 *Biochem. J.* (1995) pp. 233–241, all of which are incorporated herein by reference.

The biopotencies of the compounds of formula (I) have been studied and compared to that of 1α,25-dihydroxyvitamin $D_3$, the active hormonal form of vitamin D and the standard against which all vitamin D compounds and analogues are measured. For example, it has been found that the vitamin D receptor (VDR) binding affinities of the compounds of formula (I), or their active metabolites, are substantially equivalent to (i.e., equal to or up to 3 times weaker than) the affinity of 1α,25-dihydroxyvitamin $D_3$. Such receptor binding affinities are indicative of potent biological activity.

At the same time, it has been found that compounds of formula (I) are significantly less toxic than their corresponding vitamin $D_3$ analogues. For example, in parent co-pending application, Ser. No. 08/265,438, the disclosure of which is incorporated herein by reference, the $LD_{50}$ for 1α-hydroxyvitamin $D_4$ was found to be 1.0 mg/kg in males and 3.0 mg/kg in females, i.e., substantially less toxic than 1α-hydroxyvitamin $D_3$ ($LD_{50}$~0.2 mg/kg). Further, in the parent U.S. Pat. No. 5,403,831, and its grandparent U.S. Pat. No. 5,104,864, both of which are incorporated herein by reference, it has been shown that 1α-hydroxyvitamin $D_2$ has the same biopotency as 1α-hydroxyvitamin $D_3$ and 1α,25-dihydroxyvitamin $D_3$ but is much less toxic. Even dosages up to 10 μg/day of 1α-hydroxyvitamin $D_2$ in women with postmenopausal osteoporosis elicited only mild hypercalciuria (U.Ca>300 mg/24 hrs), and no marked hypercalcemia (S. Ca>11.0 mg/dL) solely due to 1α-hydroxyvitamin $D_2$ was evident. Additionally, the compound did not adversely affect kidney function, as determined by creatinine clearance and BUN; nor did it increase urinary excretion of hydroxyproline, indicating the absence of any stimulatory effect on bone resorption. Administration of 1α-hydroxyvitamin $D_2$ to healthy adult males in dosages up to 8 μg/day showed no clinically significant hypercalcemia or other adverse effects.

The hypocalcemic vitamin D compounds are useful as active compounds or ingredients in pharmaceutical compositions having reduced side effects and low toxicity as compared with the known analogues of active forms of vitamin $D_3$.

The pharmacologically active compounds of this invention can be processed in accordance with conventional methods of pharmacy to produce medicinal agents for administration to patients, e.g., mammals including humans. For example, the hypocalcemic vitamin D compounds of the present invention can be employed in admixtures with conventional excipients, e.g., pharmaceutically acceptable carrier substances suitable for enteral (e.g., oral), parenteral or topical application which do not deleteriously react with the active compounds.

Suitable pharmaceutically acceptable carriers include but are not limited to water, salt solutions, alcohols, gum arabic, vegetable oils (e.g., almond oil, corn oil, cottonseed oil, peanut oil, olive oil, coconut oil), mineral oil, fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring, flavoring and/or one or more other active compounds, for example, vitamin $D_3$ and its 1α-hydroxylated metabolites, conjugated estrogens or their equivalents, anti-estrogens, calcitonin, biphosphonates, calcium supplements, cobalamin, pertussis toxin and boron.

For parenteral application, particularly suitable are injectable, sterile solutions, preferably oily or aqueous solution, as well as suspensions, emulsions, or implants, including suppositories. Parenteral administration suitably includes subcutaneous, intramuscular, or intravenous injection, nasopharyngeal or mucosal absorption, or transdermal absorption. Where indicated, the compounds of formula (I) may be given by direct injection into the tumor, e.g., parathyroid adenoma, or by regional delivery by intra-arterial delivery or delivery via the portal vein. Regional delivery is especially suitable for hepatic cancers. Ampoules are convenient unit dosages.

For enteral application, particularly suitable are tablets, dragees, liquids, drops, suppositories, lozenges, powders, or capsules. A syrup, elixir, or the like can be used if a sweetened vehicle is desired.

For topical application, suitable nonsprayable viscous, semi-solid or solid forms can be employed which include a carrier compatible with topical application and having a dynamic viscosity preferably greater than water, for example, mineral oil, almond oil, self-emulsifying beeswax, vegetable oil, white soft paraffin, and propylene glycol. Suitable formulations include, but are not limited to, creams, ointments, lotions, solutions, suspensions, emulsions, powders, liniments, salves, aerosols, transdermal patches, etc., which are, if desired, sterilized or mixed with auxiliary agents, e.g., preservatives, stabilizers, demulsifiers, wetting agents, etc. A cream preparation in accordance with the present invention suitably includes, for example, mixture of water, almond oil, mineral oil and self-emulsifying beeswax; an ointment preparation suitably includes, for example, almond oil and white soft paraffin; and a lotion preparation suitably includes, for example, dry propylene glycol.

Topical preparations of the compound in accordance with the present invention useful for the treatment of skin disorders may also include epithelialization-inducing agents such as retinoids (e.g., vitamin A), chromanols such as vitamin E, β-agonists such as isoproterenol or cyclic adenosine monophosphate (cAMP), anti-inflammatory agents such as corticosteroids (e.g., hydrocortisone or its acetate, or dexamethasone) and keratoplastic agents such as coal tar or anthralin. Effective amounts of such agents are, for example, vitamin A about 0.003 to about 0.3% by weight of the composition; vitamin E about 0.1 to about 10%; isoproterenol about 0.1 to about 2%; cAMP about 0.1 to about 1%; hydrocortisone about 0.25 to about 5%; coal tar about 0.1 to about 20%; and anthralin about 0.05 to about 2%.

For rectal administration, the compound is formed into a pharmaceutical composition containing a suppository base such as cacao oil or other triglycerides. To prolong storage life, the composition advantageously includes an antioxidant such as ascorbic acid, butylated hydroxyanisole or hydroquinone.

For treatment of calcium metabolic disorders, oral administration of the pharmaceutical compositions of the present invention is preferred. Generally, the compound of this invention is dispensed by unit dosage form comprising about 0.5 µg to about 25 µg in a pharmaceutically acceptable carrier per unit dosage. The dosage of the compound according to this invention generally is about 0.01 to about 1.0 µg/kg/day, preferably about 0.04 to about 0.3 µg/kg/day. Oral dosing for the treatment of cancers and neoplasms and other hyperproliferative diseases generally is about 10 µg to 200 µg/day.

For topical treatment of skin disorders, the dosage of the compound of the present invention in a topical composition generally is about 0.01 µg to about 50 µg per gram of composition. For treatment of cancers, the dosage of hypocalcemic vitamin D compound in a locally applied composition generally is about 0.01 µg to 100 µg per gram composition.

Oral administration of the pharmaceutical compositions of the present invention is preferred. The dosage of the compounds for the treatment of cancer or neoplasms according to this invention generally is about 0.01 to about 2.0 µg/kg/day, preferably about 0.01 to about 1.0 µg/kg/day. As noted above, dosing of the hypercalcemia vitamin D compounds in accordance with the present invention can be done on an episodic basis in which higher doses can be used, generally about 20 µg to about 200 µg given once every 2–7 days. The dose can be given as a single dose or a divided dose in 4 or 5 subdoses, the subdoses given one every hour until the total dose is taken. Generally, the compounds of this invention are dispensed by unit dosage form in a pharmaceutically acceptable carrier.

Those of ordinary skill in the art will readily optimize effective doses and coadministration regimens as determined by good medical practice and the clinical condition of the individual patient. Regardless of the manner of administration, it will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on age, body weight, general state of health, on diet, on the timing and mode of administration, on the rate of excretion, and on medicaments used in combination and the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

Further, included within the scope of the present invention is the co-administration of hypocalcemic vitamin D compound with an anticancer agent, e.g., a cytotoxic agent, Such agents suitably include antimetabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophasphamide, melphalan, biochoroethylnitrosurea, hydroxyurea), platinum agents (e.g. cisplatin, carboplatin, oxaliplatin, JM-216, CI-973), anthracyclines (e.g., doxrubicin, daunorubicin), antibiolitics (e.g., mitomycin, idarubicin, adriamycin, daunomycin), topoisomerase inhibitors (e.g., etoposide, camptothecins) or any other cytotoxic agents. (estramustine phosphate, prednimustine). It is anticipated that the hypocalcemic vitamin D compounds used in combination with various anticancer drugs can give rise to a significantly enhanced cytotoxic effect on cancerous cells, thus providing an increased therapeutic effect. Specifically, as a significantly increased growth-inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the anticancer drugs used alone in larger doses. Possible dose ranges of these co-administered anticancer agents are about 0.1 to 20 mg/kg/day.

The term "co-administration" is meant to refer to any administration route in which two or more agents are administered to a patient or subject. For example, the agents may be administered together, or before or after each other. The agents may be administered by different routes, e.g., one agent may be administered intravenously while the second agent is administered intramuscularly, intravenously or orally. The agents may be administered simultaneously or sequentially, as long as they are given in a manner sufficient to allow both agents to achieve effective concentrations in the body. The agents also may be in an admixture, as, for example, in a single tablet. In sequential administration, one agent may directly follow administration of the other or the agents may be give episodically, i.e., one can be given at one time followed by the other at a later time, typically within a week. An example of a suitable co-administration regimen is where a hypocalcemic vitamin D compound is administered from 0.5 to 7 days prior to administration of a cytotoxic agent.

Also included within the scope of the present invention is the co-administration of effective dosages of the hypocalcemic vitamin D compounds in conjunction with administration of hormones or other agents, e.g., estrogens, which are known to ameliorate bone diseases or disorders. For example, prostate cancer often metastasizes to bone, causing bone loss and associated pain. Such bone agents may include conjugated estrogens or their equivalents, calcitonin, bisphosphonates, calcium supplements, cobalamin, pertussis toxin and boron. Possible dose ranges for these co-administered bone agents are provided in Table 1.

TABLE 1

Possible Oral Dose Ranges for Various Bone Agents
Co-Administered With 1α-Hydroxyvitamin D of Formula (I)

| Agent | Dose Ranges | | |
|---|---|---|---|
| | Broad | Preferred | Most Preferred |
| Conjugated Estrogens or Equivalent (mg/day) | 0.3–5.0 | 0.4–2.4 | 0.6–1.2 |
| Sodium Fluoride (mg/day) | 5–150 | 30–75 | 40–60 |
| Calcitonin (IU/day) | 5–800 | 25–500 | 50–200 |
| Bisphosphonates (mg/day) | 0.5–20 | 1–15 | 5–10 |
| Calcium Supplements (mg/day) | 250–2500 | 500–1500 | 750–1000 |
| Cobalamin (µg/day) | 5–200 | 20–100 | 30–50 |
| Pertussis Toxin (mg/day) | 0.1–2000 | 10–1500 | 100–1000 |
| Boron (mg/day) | 0.10–3000 | 1–250 | 2–100 |

Antiestrogens, such as Tamoxifen™, are also known bone agents and may be suitably used in conjunction with the hypocalcemic hydroxyvitamin D compounds of the present invention.

The present invention is further explained by the following examples which should not be construed by way of limiting the scope of the present invention.

VDR BINDING ANALYSES

EXAMPLE 1

1α,24-dihydroxyvitamin $D_2$ [1α,24-$(OH)_2D_2$]

The affinity of 1α,24-$(OH)_2D_2$ for the mammalian vitamin D receptor (VDR) was assessed using a commercially available kit of bovine thymus VDR and standard 1,25-$(OH)_2D_3$ solutions from lncstar (Stillwater, Minn.). The half-maximal binding of chemically synthesized 1α,24-$(OH)_2D_2$ was approximately 150 pg/ml whereas that of 1α,25-$(OH)_2D_3$ was 80 pg/ml. Thus, the 1α,24—$(OH)_2D_2$ had a very similar affinity for bovine thymus VDR as did 1α,25-$(OH)_2D_3$, indicating that 1α,24—$(OH)_2D_2$ has potent biological activity.

EXAMPLE 2

1α,24-dihydroxy vitamin $D_4$ [1α,24-$(OH)_2D_4$]

The VDR affinity binding of 1α,24-$(OH)_2D_4$ was investigated. The 1α,24-$(OH)_2D_4$ was incubated with vitamin D receptor and radiolabeled tracer 1α,25-$(OH)_2D_3$. After incubation, the amount of radioactivity bound to the receptor was determined and compared with the amount bound after co-incubation of unlabeled and labeled 1α,25-$(OH)_2D_3$. It was found that 50 pg/tube of 1α,24-$(OH)_2D_4$ was equivalent to approximately 20 pg 1α,25-$(OH)_2D_3$.

These results show that 1α,24-$(OH)_2D_4$ binds slightly less tightly to the vitamin D receptor than does 1α,25-$(OH)_2D_3$. Such data mean that 1α,24-$(OH)_2D_4$ has high affinity for the VDR and significant biological activity, similar to that of 1α,25-$(OH)_2D_3$. These data are consistent with gene expression studies done (described below) with 1α,24-$(OH)_2D_4$ which demonstrate that 1α,24-$(OH)_2D_4$ is only slightly less active than is 1α,25-$(OH)_2D_3$.

These results are surprising and unexpected in view of the prior art. They are contrary to the normative wisdom in the vitamin D art regarding the very low degree of biological activity of vitamin $D_4$ compounds.

EXAMPLE 3

1α,24-dihydroxyvitamin $D_2$ [1α,24-$(OH)_2D_2$]

VDR binding of vitamin D compounds by prostate cells is demonstrated using the techniques of Skowronski et al., 136 *Endocrinology* (1995) 20–26, which is incorporated herein by reference. Prostate-derived cell lines are cultured to near confluence, washed and harvested by scraping. Cells are washed by centrifugation, and the cell pellet resuspended in a buffered salt solution containing protease inhibitors. The cells are disrupted by sonication while cooling on ice. The supernatant obtained from centrifuging the disrupted cells at 207,000×g for 35 min at 4EC is assayed for binding. 200 TL of soluble extract, (1–2 mg protein/ml supernatant) is incubated with a 1 nM $^3$H-1α,25-$(OH)_2D_3$ and increasing concentrations of 1α,24-$(OH)_2$-$D_2$ (0.01–100 nM) for 16–20 hr at 4EC. Bound and free hormones are separated with hydroxylapatite using standard procedures. Specific binding is calculated by subtracting nonspecific binding obtained in the presence of a 250-fold excess of nonradioactive 1α,25-$(OH)_2D_3$ from the total binding measured. The results demonstrate that 1α,24-$(OH)_2D_2$ has strong affinity for prostate VDR, indicating that $1\alpha,24\text{-}(OH)_2D_2$ has potent biological activity in respect of prostate cells.

EXAMPLE 4

$1\alpha,24$-dihydroxy vitamin $D_4$ [$1\alpha,24\text{-}(OH)_2D_4$]

The procedure of Example 3 is repeated using the active vitamin D analogue $1\alpha,24\text{-}(OH)_2D_4$, and the specific binding is determined. The results demonstrate that $1\alpha,24\text{-}(OH)_2D_4$ has strong affinity for prostate VDR, indicating that $1\alpha,24\text{-}(OH)_2D_4$ has potent biological activity in respect of prostate cells.

EXAMPLE 5

$1\alpha,25$-dihydroxyvitamin $D_4$ [$1\alpha,25\text{-}(OH)_2D_4$]

The procedure of Example 3 is repeated using the active vitamin D analogue $1\alpha,25\text{-}(OH)_2D_4$, and the specific binding is determined. The results demonstrate that $1\alpha,25\text{-}(OH)_2D_4$ has strong affinity for prostate VDR, indicating that $1\alpha,25\text{-}(OH)_2D_4$ has potent biological activity in respect of prostate cells.

GENE EXPRESSION

EXAMPLE 6

$1\alpha,24$-dihydroxy vitamin $D_4$ [$1\alpha,24\text{-}(OH)_2D_4$]

Using the plasmids p(CT4)$^4$TKGH, a vitamin D receptor (VDR)-expressing plasmid, and pSG5-hVDR⅓, a plasmid containing a Growth Hormone (GH) gene, under the control of a vitamin D-responsive element (VDRE), experiments were conducted to explore the ability of $1\alpha,24\text{-}(OH)_2D_4$ to induce vitamin D-dependent growth hormone acting as a reporter gene compared to that of $1\alpha,25\text{-}(OH)_2D_3$. Cells in culture were transfected with these two plasmids. One plasmid contained the gene for Growth Hormone (GH) under the control of the vitamin D responsive element (VDRE) and the other plasmid contained the structural gene for the vitamin D receptor (VDR). These transfected cultures were incubated with $1\alpha,24\text{-}(OH)_2D_4$ or $1\alpha,25\text{-}(OH)_2D_3$, and the production of growth hormone was measured. Table 2 below shows the results of this assay:

TABLE 2

Induction of Growth Hormone by Vitamin D Compounds

| Compound | Concentration Used (M) | Growth Hormone Induction (ng/ml) |
|---|---|---|
| 1,25-(OH)$_2$D$_3$ | 1 × 10$^{-10}$ | 39 |
| 1,25-(OH)$_2$D$_3$ | 5 × 10$^{-10}$ | 248 |
| 1,24-(OH)$_2$D$_4$ | 5 × 10$^{-10}$ | 165 |
| 1,24-(OH)$_2$D$_4$ | 1 × 10$^{-9}$ | 628 |
| 1,24-(OH)$_2$D$_4$ | 5 × 10$^{-9}$ | 1098 |

These data show that the ability of $1\alpha,24\text{-}(OH)_2D_4$ to stimulate vitamin D-dependent growth hormone is nearly equivalent to that of $1\alpha,25\text{-}(OH)_2D_3$. Such results are truly surprising and would not have been expected by following the teachings of the prior art.

EXAMPLE 7

$1\alpha,24(S)$-dihydroxyvitamin $D_2$ and $1\alpha,24(R)$-dihydroxy-vitamin $D_2$ [$1\alpha,24(S)\text{-}(OH)_2D_2$ and $1\alpha,24(R)\text{-}(OH)_2D_2$]

The gene expression study described in Example 6 was conducted to compare the biological activity in vitro of chemically synthesized $1\alpha,24(S)\text{-}(OH)_2D_2$ and $1\alpha,24(R)\text{-}(OH)_2D_2$, with $1\alpha,25\text{-}(OH)_2D_3$ and 25-OH-D$_3$. The vitamin D-dependent transcriptional activation model system was used in which plasmids pSG5-hVDR⅓ and p(CT4)$^4$TKGH were co-transfected into Green monkey kidney, COS-1 cells.

Transfected cells were incubated with vitamin D metabolites and growth hormone production was measured. As shown in Table 3, both $1\alpha,24(S)\text{-}(OH)_2D_2$ and its epimer, $1\alpha,24(R)\text{-}(OH)_2D_2$, had significantly more activity in this system than 25-OH-D$_3$, with $1\alpha,24(S)\text{-}(OH)_2D_2$ having nearly the same activity as $1\alpha,25\text{-}(OH)_2D_3$.

TABLE 3

Vitamin D-Inducible Growth Hormone Production In Transfected COS-1 Cells

| Inducer | Molar Concentration | Total GH Production* (ng/ml) | Net vitamin DCinducible GH-production (ng/ml) |
|---|---|---|---|
| Ethanol | | 44 | 0 |
| 25-OH—D$_3$ | 1 × 10$^{-7}$ | 245 | 201 |
| | 1 × 10$^{-6}$ | 1100 | 1056 |
| | 1 × 10$^{-5}$ | 775 | 731 |
| 1α,25-(OH)$_2$D$_3$ | 1 × 10$^{-10}$ | 74 | 30 |
| | 1 × 10$^{-9}$ | 925 | 881 |
| | 1 × 10$^{-8}$ | 1475 | 1441 |
| 1α,24(S)-(OH)$_2$D$_2$ | 5 × 10$^{-10}$ | 425 | 381 |
| | 5 × 10$^{-9}$ | 1350 | 1306 |
| | 5 × 10$^{-8}$ | 1182 | 1138 |
| 1α,24(R)-(OH)$_2$D$_2$ | 1 × 10$^{-9}$ | 80 | 36 |
| | 1 × 10$^{-8}$ | 1100 | 1056 |
| | 1 × 10$^{-7}$ | 1300 | 1256 |

*Averages of duplicate determinations

INHIBITION OF CELL PROLIFERATION

EXAMPLE 8

$1\alpha,24$-dihydroxyvitamin $D_2$ [$1\alpha,24\text{-}(OH)_2D_2$]

Inhibition of cell proliferation is demonstrated using the techniques of Skowronski et al., 132 *Endocrinology* (1993) 1952–1960 and 136 *Endocrinology* (1995) 20–26, both of which are incorporated herein by reference. The cell lines, LNCaP and PC-3, which are derived from human prostate adenocarcinoma, are seeded in six-well tissue culture plates at a density of about 50,000 cells/plate. After the cells have attached and stabilized, about 2–3 days, the medium is replenished with medium containing vehicle or the active vitamin D analogue $1\alpha,24\text{-}(OH)_2D_2$, at concentrations from $10^{-11}$ M to $10^{-7}$ M. Medium containing test analogue or vehicle is replaced every three days. After 6–7 days, the medium is removed, the cells are rinsed, precipitated with cold 5% trichloroacetic acid, and washed with cold ethanol. The cells are solubilized with 0.2 N sodium hydroxide, and the amount of DNA determined by standard procedures. The results show that cultures incubated with $1\alpha,24\text{-}(OH)_2D_2$ in accordance with the present invention have significantly fewer cells than the control cultures.

EXAMPLE 9

$1\alpha,24$-dihydroxy vitamin $D_4$ [$1\alpha,24\text{-}(OH)_2D_4$]

The procedure of Example 8 is repeated using the active vitamin D analogue $1\alpha,24\text{-}(OH)_2D_4$, and the cell number is determined. Cultures incubated with 1α,24-(OH)$_2$D$_4$ have significantly fewer cells than the control cultures.

EXAMPLE 10

1α,25-dihydroxyvitamin D$_4$ [1α,25-(OH)$_2$D$_4$]

The procedure of Example 8 is repeated using the active vitamin D analogue 1α,25-(OH)$_2$D$_4$, and the cell number is determined. Cultures incubated with 1α,25-(OH)$_2$D$_4$ have significantly fewer cells than the control cultures.

STIMULATION OF CELL DIFFERENTIATION

EXAMPLE 11

1α,24-dihydroxyvitamin D$_2$ [1α,24-(OH)$_2$D$_2$]

Using the techniques of Skowronski et al., 132 *Endocrinology* (1993) 1952–1960 and 136 *Endocrinology* (1995) 20–26, both of which are incorporated herein by reference, cells of the cell line, LNCaP, which is derived from a human metastatic prostate adenocarcinoma and known to express PSA, are seeded in six-well tissue culture plates at a density of about 50,000 cells/plate. After the cells have attached and stabilized, about 2–3 days, the medium is replenished with medium containing vehicle or the active vitamin D analogue, 1α,24-(OH)$_2$D$_2$, at concentrations from $10^{-11}$ M to $10^{-7}$ M. After 6–7 days, the medium is removed and stored at –20EC for prostate specific antigen (PSA) analysis.

The cells from parallel cultures are rinsed, precipitated, and the amount of DNA determined by standard procedures. PSA is measured by standard known methods. Cultures incubated with 1α,24-(OH)$_2$D$_2$ have significantly more PSA than control cultures when expressed as mass of PSA/cell.

EXAMPLE 12

1α,24-dihydroxyvitamin D$_4$ [1α,24-(OH)$_2$D$_4$]

The procedure of Example 12 is repeated except the active vitamin D analogue is 1α,24-(OH)$_2$D$_4$. The PSA is measured and cultures incubated with 1α,24-(OH)$_2$D$_4$ have significantly more PSA than control cultures when expressed as mass of PSA/cell.

EXAMPLE 13

1α,25-dihydroxyvitamin D$_4$ [1α,24-(OH)$_2$D$_4$]

The procedure of Example 12 is repeated except the active vitamin D analogue is 1α,25-(OH)$_2$D$_4$. The PSA is measured and cultures incubated with 1α,25-(OH)$_2$D$_4$ have significantly more PSA than control cultures when expressed as mass of PSA/cell.

EXAMPLE 14

Inhibition of VEGF-Induced Endothelial Cell Proliferation

A vitamin D compound of formula (I) inhibition of VEGF-induced endothelial cell proliferation is demonstrated using the techniques of Mantell et al., *Circulation Research* (Aug. 4, 2000), 214–220.

The compound of formula I, e.g., 1α,24-dihydroxyvityamin D$_2$, is added to semiconfluent Bovine aortic endothelial cells (BAECs) cultered in the presence of VEGF, and the effects of these factors on cell proliferation are determined. The BAECs are plated at $0.5 \times 10^5$ cells per 35-mm dish. After 24 hours, cultures are incubated with and without VEGF (20 ng/mL) and 1α,24-dihydroxyvityamin D$_2$ in 2% FCS-MEM. Cell numbers are determined on days 1 and 6. The results showed that the simultaneous addition of 1α,24-dihydroxyvityamin D$_2$ and VEGF significantly inhibits the morphogenetic effect of this growth factor in a dose-dependent manner. The few sprouting cells that are present are less elongated than those formed in the absence of 1α,24-dihydroxyvityamin D$_2$, and these cells remain isolated and do not combine into networks.

EXAMPLE 15

Inhibition Angiogenesis In Vitro

Using the technique of Mantell et al., *Circulation Research* (Aug. 4, 2000), 214–220, confluent BAECs are incubated with VEGF (20 ng/mL) with or without 1α,24-dihydroxyvityamin D$_2$ mol/L) for 15 days. Five replicate experiments are performed: control culture, culture incubated with VEGF, culture incubated with 1α,24-dihydroxyvityamin D$_2$ plus VEGF, and culture incubated with 1α,24-dihydroxyvityamin D$_2$. Also, in a dose controlled experiment, confluent BAECs are incubated with 2% FCS-MEM (control) with or without 1α,24-dihydroxyvityamin D$_2$, control culture, $1 \times 10^{-7}$ mol/L 1α,24-dihydroxyvityamin D$_2$, VEGF (20 ng/mL), VEGF plus 1α,24-dihydroxyvityamin D$_2$, VEGF plus 1α,24-dihydroxyvityamin D$_2$, and VEGF plus 1α,24-dihydroxyvityamin D$_2$, and the area occupied by elongated sprouting cells is quantified. Control endothelial cells remain as monolayers of polygonal cells, characteristic of the "resting" phenotype of quiescent endothelial cells. A small number of single, elongated, sprouting cells appear in the control cultures as the experiment progresses; however, these cells remained isolated and few in number. VEGF induces the formation of sprouting elongated cells underneath the cobblestone monolayer that combine to form networks of interconnected multicellular cords. The simultaneous addition of 1α,24-dihydroxyvityamin D$_2$ and VEGF significantly inhibit the morphogenetic effect of this growth factor in a dose-dependent manner. The few sprouting cells that were present are less elongated than those that form in the absence of 1α,24-dihydroxyvityamin D$_2$, and these cells remain isolated and do not combine into networks. The addition of 1α,24-dihydroxyvityamin D$_2$ alone inhibits the formation of endothelial cell sprouts in control medium.

EXAMPLE 16

Induction of Apoptosis of Sprouting Endothelial Cells

Apoptosis is ascertained by detecting DNA strand breaks by using an in situ cell death assay, terminal deoxynucleotidyl transferase-mediated dUTP nick end-labeling (TUNEL) using the technique of Mantell et al., *Circulation Research* (Aug. 4, 2000), 214–220. BAECs are incubated with VEGF for 4 days. VEGF is then withdrawn, and cultures are incubated with or without 1α,24-dihydroxyvityamin D$_2$ for 66 hours. Cells are fixed, and apoptosis was assessed by TUNEL Limited regression of sprouting cells is observed in control cultures. Nuclei of sprouting endothelial cells are generally negative for DNA fragmentation, as indicated by low TUNEL staining. The addition of 1α,24-dihydroxyvityamin D$_2$ to VEGF-stimulated cultures results in a high number of nuclei that are positive for DNA fragmentation. Stained nuclei are specifically associated with the population of sprouting endothelial cells; no staining $^i$ observed in the cobblestone monolayer.

EXAMPLE 17

Inhibition of Angiogenesis In Vivo

The effect of 1α,24-dihydroxyvityamin $D_2$ on the formation of microvessels in vivo is examined by using a model in which MCF-7 breast carcinoma cells that are induced to overexpress $VEGF_{121}$ (VEGF transfectants) are xenografted subcutaneously together with MDA-435S breast carcinoma cells into nude mice e.g., female BALC/C nu/nu mice.

Tumors are formed in all of the mice injected with VEGF transfectants. Immunohistochemistry using a rat anti-CD31 antibody is used to assess the vascularity of the tumors produced in these mice. Clusters of small capillaries are present in all tumors. However, treatment with 1α,24-dihydroxyvityamin $D_3$ produces tumors that appeared less vascularized than tumors formed in mice treated with vehicle alone. In addition, large capillaries are evident in tumors formed in control animals; these are never observed in tumors formed after treatment with 1α,24-dihydroxyvityamin $D_2$. Tumor volume is not significantly altered, and the proportion of MCF7 and MDA-435S cells present in the tumors is not different in mice treated with 1α,24-dihydroxyvityamin $D_3$ compared with those treated with vehicle alone.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation lawfully accorded the appended claims.

What is claimed is:

1. A method of inhibiting angiogenesis associated with malignant or neoplastic cells, comprising treating the cells with an effective amount of a hypocalcemic hydroxy vitamin D compound having a hydrocarbon moiety at the $C_{24}$ position, the cells being cancers of the breast, colon, prostate, testes, lung, neck and head, pancreas, endometrium, bladder, cervix, ovaries, squamous cell carcinomas, myeloid and lymphocytic leukemia, lymphoma, medullary thyroid carcinoma, melanoma, multiple myeloma, retinoblastoma or sarcomas of the soft tissues and bone.

2. A method of inhibiting angiogenesis associated with malignancy or neoplasm in a subject in need thereof, comprising administering to the subject an effective amount of a hypocalcemic vitamin D compound represented by formula I:

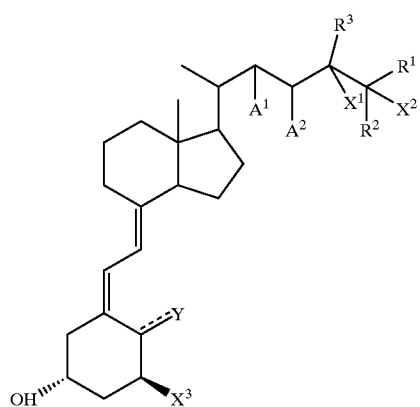

(I)

wherein $A^1$ and $A^2$ each are hydrogen or a carbon—carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, and $X^2$ is hydrogen or hydroxyl, or, may be taken with $R^1$ or $R^2$, to constitute a double bond, and $X^3$ is hydrogen or hydroxyl provided that at least one of $X^1$, $X^2$ and $X^3$ is hydroxyl; and Y is a methylene group if the bond to Y is a double or is a methyl group or hydrogen if the bond to Y is a single bond sufficient to inhibit angiogenesis of the malignancy or neoplasm.

3. A method in accordance with claim 2, wherein the hypocalcemic vitamin D compound is represented by formula II:

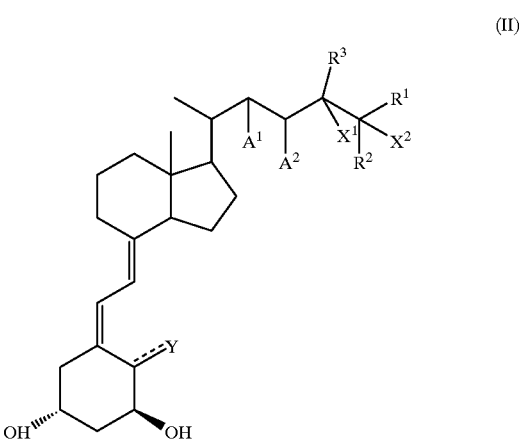

(II)

wherein $A^1$ and $A^2$ each are hydrogen or a carbon—carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, and $X^2$ is hydrogen or hydroxyl, or, may be taken with $R^1$ or $R^2$, to constitute a double bond, and Y is a methylene group if the bond to Y is a double or is a methyl group or hydrogen if the bond to Y is a single bond.

4. The method of claim 2, wherein said hypocalcemic vitamin D is a 1α-hydroxyvitamin D compound is represented by formula III:

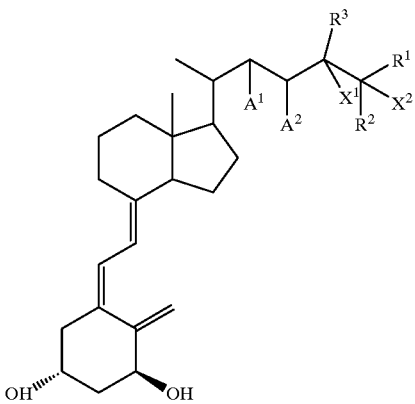

(III)

wherein $A^1$ and $A^2$ each are hydrogen or a carbon—carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, and $X^2$ is hydrogen or hydroxyl, or, may be taken with $R^1$ or $R^2$, to constitute a double bond.

5. The method of claim 4, wherein the compound of formula (I) is 1α,24-dihydroxyvitamin $D_2$, 1α,24-dihydroxyvitamin $D_4$, 1α,25-dihydroxyvitamin $D_2$, 1α,25-dihydroxyvitamin $D_4$, 1α-hydroxyvitamin $D_2$ or 1α-hydroxyvitamin $D_4$.

6. A method in accordance with claim 2, wherein a dosing regimen for the hypocalcemic vitamin D compound is a daily regimen or an episodic regimen.

7. A method in accordance with claim 6, wherein the espisodic regimen is a dose once every 2 to 7 days.

8. A method in accordance with claim 6, wherein the hypocalcemic vitamin D compound is administered daily at a dose of about 10 to 100 μg/day.

9. A method in accordance with claim 6, wherein the hypocalcemic vitamin D compound is administered orally, is administered intravenously, is injected directly into a cancer site, or is regionally delivered to a cancer site.

10. A method in accordance with claim 9, wherein the hypocalcemic vitamin D compound is administered orally.

11. A method in accordance with claim 2, wherein the hypocalcemic vitamin D compound is co-administered with a cytotoxic agent.

12. A method in accordance with claim 11, wherein the cytotoxic agent is an antimetabolite, and antimicrotubule agent, an alkyating agent, a platinum agent, an anthracycline, a topoisomase inhibitor, or an antibiotic.

13. A method in accordance with claim 12, wherein the antimetabolite is 5-fluorouracil, methotrexate or fludarabine.

14. A method in accordance with claim 12, wherein the antimicrotubule agent isvincristine, vinblastine or a taxane.

15. A method in accordance with claim 11, wherein the taxane is paclitaxel or docetaxel.

16. A method in accordance with claim 12, wherein the alkylating agent is cyclophasphamide, melphalan, biochoroethylnitrosurea or hydroxyurea.

17. A method in accordance with claim 12, wherein the platinum agent is cisplatin, carboplatin, oxaliplatin, JM-216 or CI-973.

18. A method in accordance with claim 12, wherein the anthracycline is doxrubicin or daunorubicin.

19. A method in accordance with claim 12, wherein the antibiotic is mitomycin, idarubicin, adriamycin or daunomycin.

20. A method in accordance with claim 12, wherein the topoisomerase inhibitior is etoposide or camptothecins.

21. A method in accordance with claim 12, wherein the cytotoxic agent is estramustine phosphate or prednimustine.

22. A method of treating a human to inhibit angiogenesis associated with breast cancer, colon cancer, prostate cancer, testicular cancer, pancreatic cancer, endometrial cancer, small cell and non-small cell cancer of the lung (including squamous, adneocarcinoma squamous cell of the head and neck, bladder, ovarian and cervical cancers, myeloid and lymphocyltic leukemia, lymphoma, hepatic tumors, medullary thyroid carcinoma, multiple myeloma, melanoma, retinoblastoma or sarcomas of the soft tissue and bone, comprising administering to the human an effective amount of a hypocalcemic vitamin D compound.

23. A method of claim 22, wherein said hypocalcemic vitamin D is a 1α-hydroxyvitamin D compound represented by formula III:

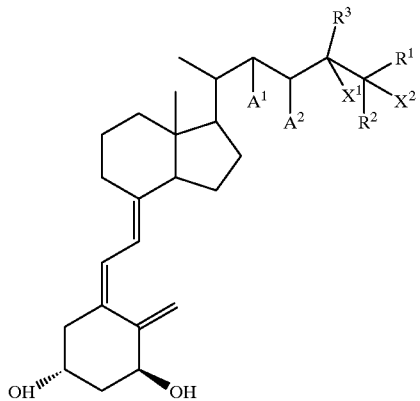

(III)

wherein $A^1$ and $A^2$ each are hydrogen or a carbon—carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, and $X^2$ is hydrogen or hydroxyl, or, may be taken with $R^1$ or $R^2$, to constitute a double bond.

24. The method of claim 23, wherein said therapeutic amount is 0.01 μg/kg/day to 2.0 μg/kg/day.

25. The method of claim 23, wherein the compound of formula (I) is 1α,24-dihydroxyvitamin $D_2$, 1α,24-dihydroxyvitamin $D_4$,1α25-dihydroxyvitamin $D_2$, 1α,25-dihydroxyvitamin $D_4$, 1α-hydroxyvitamin $D_2$ or 1α-hydroxyvitamin $D_4$.

26. A method of treating a human to inhibit angiogenesis associated with malignant cells, comprising administering to the patient a hypocalcemic vitamin D compound and a cytotoxic agent.

27. A method in accordance with claim 26, wherein the hypocalcemic vitamin D compound is administered from 0.5 to 7 days prior to administration of the cytotoxic agent.

28. A method in accordance with claim 26, wherein the hypocalcemic vitamin D compound is administered 2 to 4 days prior to administration of the cytotoxic agent.

29. A method of claim 26, wherein said hypocalcemic vitamin D is a 1α-hydroxyvitamin D compound represented by formula III:

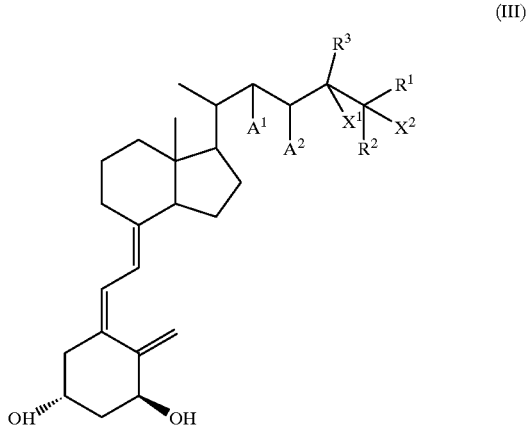

(III)

wherein $A^1$ and $A^2$ each are hydrogen or a carbon—carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, or, taken with $R^3$, constitutes a bond when $R^3$ is an alkenyl group, and $X^2$ is hydrogen or hydroxyl, or, taken with $R^1$ or $R^2$, constitutes a double bond.

30. The method of claim 29, wherein said therapeutic amount is 0.01 μg/kg/day to 2.0 μg/kg/day.

31. The method of claim 29, wherein the compound of formula (I) is 1α,24-dihydroxyvitamin $D_2$, 1α,24-dihydroxyvitamin $D_4$, 1α,25-dihydroxyvitamin $D_2$, 1α,25-dihydroxyvitamin $D_4$, 1α-hydroxyvitamin $D_2$ or 1α-hydroxyvitamin $D_4$.

32. A method in accordance with claim 29, wherein the cytotoxic agent is an antimetabolite, and antimicrotubule agent, an alkyating agent, a platinum agent, an anthracycline, a topoisomase inhibitor, or an antibiotic.

33. A method of inducing apoptosis of malignant or neoplastic cells, comprising treating the cells with an effective amount of a hypocalcemic vitamin D compound, the cells being cancers of the breast, colon, prostate, testes, lung, neck and head, pancreas, endometrium, bladder, cervix, ovaries, squamous cell carcinoma, myeloid and lymphocytic leukemia, lymphoma, medullary thyroid carcinoma, melanoma, multiple myeloma, retinoblastoma or sarcomas of the soft tissues and bone.

34. A method of inducing the regression of tumor cells comprising treating the cells with an effective amount of a hypocalcemic vitamin D compound, which inhibits angeogenesis associated with malignancy the cells being cancers of the breast, colon, prostate, testes, lung, neck and head, pancreas, endometrium, bladder, cervix, ovaries, squamous cell carcinoma, myeloid and lymphocytic leukemia, lymphoma, medullary thyroid carcinoma, melanoma, multiple myeloma, retinoblastoma or sarcomas of the soft tissues and bone.

* * * * *

UNITED STATES PATENT AND TRADEMARK OFFICE
CERTIFICATE OF CORRECTION

PATENT NO. : 6,573,256 B2  Page 1 of 1
DATED : June 3, 2003
INVENTOR(S) : Charles W. Bishop et al.

It is certified that error appears in the above-identified patent and that said Letters Patent is hereby corrected as shown below:

Title page,
Item [56], References Cited, FOREIGN PATENT DOCUMENTS, "WO 01/22974" should read -- WO 01/22974 A1 --.
OTHER PUBLICATIONS, "Sjoden et al.," reference, "N. Brautbar, "Osteoporosis: Is 1,25-$(OH)_2$D of Value in Treatment?" *Nephron* 44, 1986, pp. 161-166." should read -- N. Brautbar, "Osteoporosis: Is 1,25-$(OH)_2D_3$ of Value in Treatment?" *Nephron* 44, 1986, pp. 161-166. --.
"D.R. Crump et al.," reference, "Chemical Abstracts, vol. 113, No. 1, Jul. 1990, Columbus, Ohio, US; abstract No. 6683y, Y. Tachibana, 'Preparation of 1 beta-hydroxyvitamin $D_2$ and $D_3$,' p.6688; column 2; abstract & JP-A-02 011 563 (Nisshin Flour Milling Co.)." should read -- Chemical Abstracts, vol. 113, No. 1, 2 Jul. 1990, Columbus, Ohio, US; abstract No. 6683y, Y. Tachibana, Preparation of 1 beta-hydroxyvitamin $D_2$ and $D_3$,' p.6688; column 2; abstract & JP-A-02 011 563 (Nisshin Flour Milling Co.). --.
"* Knutson, et al.," reference, "Metabolism of 1 α-Hydroxyvitamin $D_2$ to activated Dihydroxyvitamin $D_2$Metabolites Decreases Endogenous 1α,25-Dihydroxyvitamin $D_3$ in Rats and Monkeys", *Endocrinology,* vol. 136, 11:4749-4753 (1995)." should read -- "* Knutson, et al., "Metabolism of 1 α-Hydroxyvitamin $D_2$ to activated Dihydroxyvitamin $D_2$ Metabolites Decreases Endogenous 1α,25-Dihydroxyvitamin $D_3$ in Rats and Monkeys", *Endocrinology,* vol. 136, 11:4749-4753 (1995). --.

Signed and Sealed this

Second Day of March, 2004

JON W. DUDAS
*Acting Director of the United States Patent and Trademark Office*